United States Patent [19]

Arpaio, Jr. et al.

[11] Patent Number: 4,602,900
[45] Date of Patent: Jul. 29, 1986

[54] MICRO DRILL WITH MODIFIED DRILL POINT

[76] Inventors: Jerry Arpaio, Jr., 712 Sharon Dr.; Derek E. Heath, 1917 Sherwood Dr., both of Johnson City, Tenn. 37601

[21] Appl. No.: 535,644

[22] Filed: Sep. 26, 1983

Related U.S. Application Data

[63] Continuation-in-part of Ser. No. 292,797, Aug. 14, 1981, abandoned, which is a continuation-in-part of Ser. No. 184,645, Sep. 16, 1980, Pat. No. 4,538,989, which is a continuation-in-part of Ser. No. 80,695, Oct. 1, 1979, abandoned.

[51] Int. Cl.[4] .............................................. B23B 51/02
[52] U.S. Cl. .................................................... 408/230
[58] Field of Search ............... 408/230, 199, 715, 229, 408/227; 433/102

[56] References Cited

U.S. PATENT DOCUMENTS

| | | | |
|---|---|---|---|
| 1,069,930 | 8/1913 | Down | 408/230 X |
| 2,035,298 | 3/1936 | Caldwell . | |
| 2,084,737 | 6/1937 | Magnus . | |
| 2,328,629 | 9/1943 | Eich et al. | 418/230 |
| 2,769,355 | 11/1956 | Crisp | 408/230 |
| 2,897,695 | 8/1959 | Winslow . | |
| 2,966,081 | 12/1960 | Kallio | 408/715 |
| 3,058,199 | 10/1962 | Cave et al. . | |
| 3,411,386 | 11/1968 | Kubicek . | |
| 3,443,459 | 5/1969 | Mackey et al. | 408/230 |
| 3,751,176 | 8/1973 | Von Hollen . | |
| 3,778,180 | 12/1973 | Ostrom . | |
| 3,933,075 | 1/1976 | Peterson . | |
| 3,947,143 | 3/1976 | Gulla . | |
| 3,991,454 | 11/1976 | Wale . | |
| 4,135,847 | 1/1979 | Hemmings . | |
| 4,209,275 | 6/1980 | Kim . | |
| 4,330,229 | 5/1982 | Croydon . | |

FOREIGN PATENT DOCUMENTS

| | | |
|---|---|---|
| 1419624 | 12/1975 | United Kingdom . |
| 2035806A | 6/1980 | United Kingdom . |
| 622588 | 9/1978 | U.S.S.R. . |
| 715238 | 2/1980 | U.S.S.R. . |

OTHER PUBLICATIONS

*Metal Cutting Tool Handbook*, Jul. 1965 pp. 45–55.

*Primary Examiner*—William R. Briggs
*Attorney, Agent, or Firm*—Luedeka & Neely

[57] ABSTRACT

The specification discloses a micro drill with a modified point in which the drill is formed from a rigid cylinder and has two opposed helical wings and helical edges. Each wing has an undercut leading surface to provide a positive rake angle at the helical edges of the wings, and the two wings have a smooth "S" shaped cross-section. Two opposed flanks are formed by an inclined cut in each of the wings providing the drill point with a somewhat V-shape, and a leading corner is defined on each of the wings at the intersection of the helical edge and the flanks. A cut is provided in each of the leading surfaces adjacent to and below the flanks thereby forming a cutting edge on the drill point with an increased positive cutting action. The drill may be cut so that an under-surface is formed immediately below each flank and its cutting edge and so that a side surface is formed in the wings in an orientation perpendicular to the under-surface.

4 Claims, 13 Drawing Figures

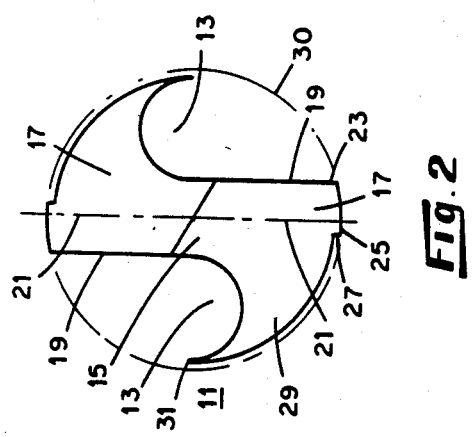
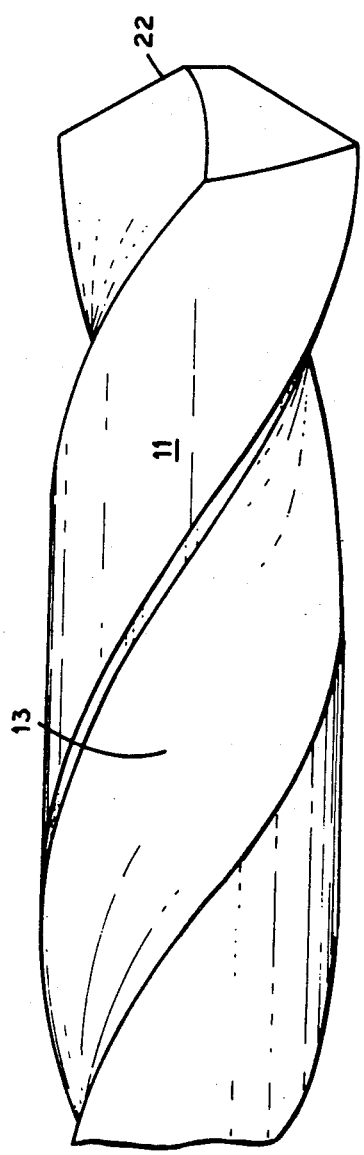

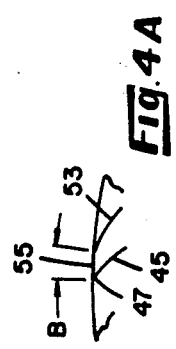
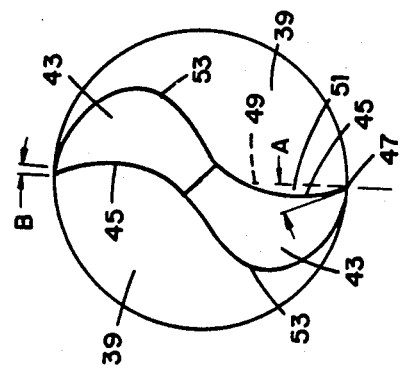
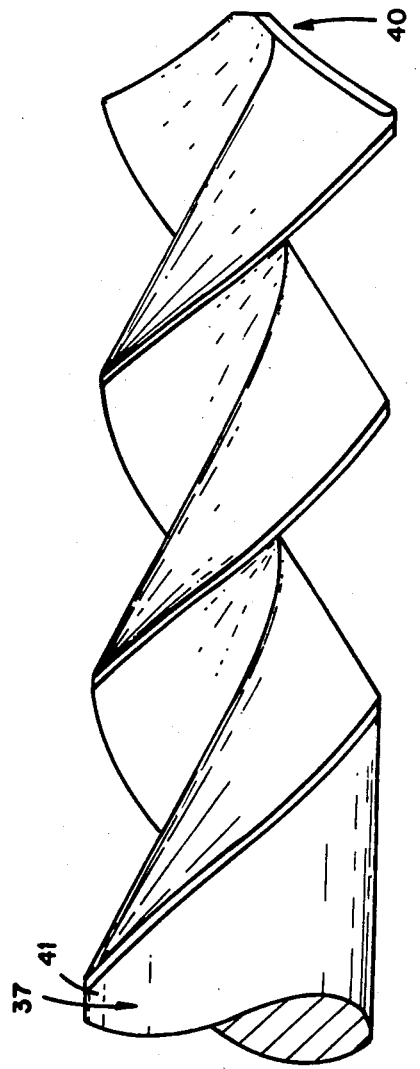

MICRO DRILL WITH MODIFIED DRILL POINT

This is a continuation-in-part of our application Ser. No. 292,797, filed Aug. 14, 1981, now abandoned, which is a continuation-in-part of our application Ser. No. 184,645, filed Sept. 16, 1980, now U.S. Pat. No. 4,538,989, which is a continuation-in-part of Ser. No. 80,695, filed Oct. 1, 1979, now abandoned.

The present invention relates to micro drills and more particularly relates to micro drills with modified points which are adapted for drilling holes of a diameter of approximately less than 0.125 inches and usually less than 0.050 inches.

Micro drills generally range in diameter size from about 0.125 inches to about 0.002 inches and are employed for many precision drilling purposes. For example, micro drills are used to drill holes in a variety of materials ranging from plastics to hard metals in such articles as printed circuit boards, cameras, watches, carburetors. fuel injectors and the like. All of these devices require precisely dimensioned holes or apertures.

The micro drill of the present invention has a modified point that provides fast and precise drilling and outstanding drill life and a body designed to rapidly remove chips. It has long been recognized that the life of a drill and its drilling characteristics are related to the shape of its point. Many drills have flanks at their points intersecting at the center of the drill to form a chisel edge. It is known that some forms of "point thinning" by cutting away part of the drill point will increase the life of the drill and numerous types of thinned drill points have been used. It has been suggested that the removal of a portion of the trailing edges of a drill point immediately adjacent to the chisel edge, without cutting away any of the chisel edge or the leading edge, results in the most durable and long lasting drill point.

Drill wobble, galling, abrasion, and burring are often encountered in the use of micro drills, and these problems also may often be related to the efficiency of the drill or drill point in initially cutting chips of material from the work piece and removing the chips of material from the work face as the drilling process continues. In using a micro drill, the chip sizes are necessarily very small, and, because of their samll size, the chips often get between the work piece and the drill and, thus, interfere with the drilling operation. The chips may cause galling, burring, abrasion and inefficiency during the drlling operation, and chips that work themselves back onto the work face of the drilled material may cause a skipping action, referred to as "heeling", at the work face which will directly interfere with the cutting ability of the drill. Generally, reduced drilling efficiency as described above, necessarily reduces the effective life of the drill.

These problems are alleviated, in part, in the present invention by providing a drill with an improved cutting action at the drill point and by providing a drill body with effective chip removal characteristics. Such improved cutting action results from a thinning of the drill point with a planar cut that removes portions of both the leading and trailing edges of the drill flanks and that produces an increased positive cutting angle at the cutting edge of the drill point. In one form of the present invention, an improved micro drill includes a rigid cylindrical body having a center axis of rotation. A drill point is formed on one end of the body and two oppositely disposed flutes helically extend from the drill point along the body. Such flutes define two opposed helically extending wings along the drill body, and each wing has a leading surface in relation to the directon of rotation of the drill and a trailing surface. The trailing surface of one of the wings is connected with the leading surface of the other of the wings. A helical edge is formed along the outermost positions of each of the leading surface.

The drill point includes two opposed flanks formed by inclined cuts in each of the wings where such cuts extend from the center axis of rotation of the cylindrical body in a downward and outward direction toward the periphery of the cylindrical body. The inclined cuts provide the drill point with a somewhat V-shape. A leading corner is defined on each of the wings at the intersection of the helical edge and the flank, and a cut is provided in each of the leading surfaces adjacent to and below the flanks and removing at least a leading portion of said flanks. The leading cuts and the inclined cuts intersect to define cutting edges on said drill point.

In the preferred embodiment, the cut forms a planar under-surface in each leading surface extending from the center of the drill point to the leading corner. This planar under-surface forms an acute angle with the flank and preferably provides a positive cutting action at the cutting edge of the drill point. Thus, the cut removes a portion of each flank along its leading or cutting edge and removes a portion of each wing along its leading surface.

In the preferred embodiment, the cut in the drill point also defines a planar side surface that is formed in each of the trailing surfaces and the connected leading surfaces of the wings. The planar side surface also intersects the flanks, and a trailing portion of the flanks and wings is removed along the planar side surface.

The cuts in the drill point of the present invention provides increased drilling efficiency by producing an increased positive cutting action at the work face. That is, the cuts at their intersections with the flanks forms a cutting edge with a more acute angle than drlls without such cut. The more acute angle results in a more positive cutting action, a more efficient cutting action and improved chip lifting action at the cutting edge. By more efficiently cutting and lifting the chips away from the work face, the chips are removed from the work piece more easily and are less likely to interfere with the cutting action of the drill. The cut also reduces, relative to uncut drills, the area of the flanks by removing a leading portion and a trailing portion from each of the flanks. The reduced area of the flanks will reduce the tendency of the drill to skip or heel at the work face and will reduce the possibility of a galling action being set up at the work face.

Since the drill point as described above results in an efficient fast cut at the work face and good initial removal of chips away from the workface, it becomes important that the chips be carried out of the hole efficiently. To achieve efficient chip removal, the drill of the present invention may include two opposed helical wings that define a drill body having a generally S-shaped transverse cross-section with the wings each having a leading surface and a trailing surface relative to the direction of rotation of the drill. The leading surfaces are formed in substantially continuous smooth concave curves; the trailing surfaces are substantially continuous smooth convex curves; and each leading surface meets one of the trailing surfaces forming a smooth transition between the two surfaces. A circumferential land is formed on each wing extending from and trailing the helical edge of each wing and subtending a radial arc of less than about 12° from the center axis of the drill. A helical channel is formed in each leading surface so that it trails a radius of the drill over a substantial portion of the radial dimension of the drill, and an undercut is formed in each of said leading surfaces so that said helical edge has a positive rake and makes an angle from about 5° to about 30° to a radius of the drill. The undercut, the channel, the smooth transition and the smooth curvature of the leading and trailing surfaces act cooperatively with each other and with the drill point to efficiently and effectively remove chips from the hole. The small land size facilitates chip removal by reducing heat in the hole and reducing the likelihood that a chip will be picked up and welded to the lands or the wings. In this construction, a reliable, efficient, fast, and long lasting drill is achieved.

The present invention may best be understood by reference to the following detailed description of a preferred embodiment of the present invention when considered in conjunction with the accompanying drawings in which:

FIG. 1 is a fragmentary side view of a drill embodying the drill body construction which is ordinarily employed in the prior art;

FIG. 2 is an end view of the drill shown in FIG. 1;

FIG. 3 is a side view of a drill embodying various features of the invention but having a conventional point;

FIG. 4 is an end view of a drill shown in FIG. 3;

FIG. 4A is a fragmentary enlargement of a portion of FIG. 4;

Figure 6:
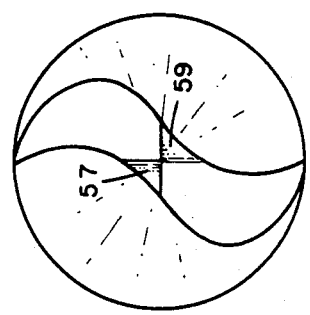
FIG. 6 is an end view of the drill shown in FIG. 5.

By way of explanation, FIGS. 1 and 2 illustrate a drill 11 having the usual prior art configuration; FIGS. 3-6 illustrate a drill having a body 37 formed in accordance with the present invention but having conventional points; and FIGS. 7-12 illustrate a drill point 111 embodying an aspect of the present invention. The drill 11 is made from a length of cylindrical stock which is provided with a pair of opposed helical flutes 13 which provides a drill body or web 15 having a pair of opposed wings 17. Each of the wings 17 includes a face 19 which is parallel to a radius 21 of the drill and is positioned ahead of the radius 21 based upon the direction of rotation of the drill. The cutting action of the drill is accomplished by the drill tip 22 and by a so-called chisel edge 23 at the peripheral edge of the face 19 insofar as concerns the outer diameter of the hole being drilled. Rearwardly (with reference to the direction of rotation of the drill) from the chisel edge 23, the wing 17 is provided with a land 25 which provides a circumferential arcuate area which determines the diameter of the drill. The land 25 follows the helical path of each of the flutes 13 up to the shank of the drill.

At the rearward end of the land (with reference to the direction of the rotation of the drill) an inwardly directed step 27 is provided and the remainder or heel 29 of the wing 17 follows the curvature of the path 30 of the chisel edge 23 but is inwardly spaced therefrom as illustrated. The distance from the chisel edge 23 to the end 31 of the heel 29 is normally of the order of about 90° of arc or more. From the end 31 of the heel 29, the wing is defined by a concave surface 33, which merges in to the face 19 of the opposite wing.

The point 22 of the drill is sharpened in the usual manner with a point angle of from about 90° to 120°, this angle varying in the manner known to the art depending upon the material being drilled.

As pointed out above, the usual drill is provided with a back taper so that the diameter across the lands 25 at the tip of the drill is larger than the diameter across the lands adjacent the shank. This is known as "back taper" and is employed to reduce the friction between the lands 25 and the wings 17 against the sides of the hole at points remote from the tip 22.

Such a construction is satisfactory for drills of larger sizes. However, in smaller sizes, such as the microdrills contemplated by this invention, i.e., drills ranging in diameter from 0.125 to 0.002 inches, such a construction causes a number of problems. For example, the face 19 of the wing 17 forms an acute angle with the wall of the hole indicated by the dotted line 30 which is the path of the chisel edge 23 in FIG. 2, so that as the drill turns and the chips are forced out of the hole being drilled, they are constantly wedged between the wall of the hole and the land 25 causing galling of the wall. In the small drill sizes, galling is extremely undesirable because it can destroy tolerances. The galling problem is aggravated at positions remote from the tip because of the back taper. Also, it has been found that with small diameter drills the fine drill particles tend to build up on the face of the heel 29 of the wing 17, especially in the area of the step 27 causing additional friction between the drill wing 17 and the side of the hole. All of this results in additional friction which increases the amount of torque required to turn the drill as well as in increased heat both of which shortens drill life and increases the tendency for the drill to break. Also, any uneven distribution of chips in the relieved area between the heels 29 and the innersurface of the hole may cause the drill to wobble and may result in a hole which is not true as does the passage of the particles between the chisel edge and the wall of the hole.

The back taper of the normal drill construction is also a problem in the small sizes. As pointed out above, the drill has a larger diameter at the tip than adjacent the shank. As a result, the hole does not fully support the sides of the drill at a point remote from the tip. Thus, the walls of the hole which has been drilled does not aid in preventing bowing of the drill which is always a problem in the smaller sizes.

FIGS. 3 and 6 illustrate various features of the present invention relating to the drill body. In general, the body of our improved micro twist drill comprises a rigid cylindrical body having two oppositely disposed flutes helically extending from the drill point along the cylindrical body towards the shank which defines a pair of oppositely disposed helically extending wings. Each of the wings has a leading surface in relation to the direction of rotation of the drill, the leading surface being undercut to provide a peripheral, positive rake helical edge which makes an angle of from about 5° to about 30° to a radius of the cylindrical body which extends to the helical edge. The wings are symmetrically disposed relative to one another to provide a drill body or web which is in transverse cross-section of generally "S" shape. The leading surface of each wing is provided with a channel, a substantial portion of which trails (relative to the direction of rotation of the drill), a line between the helical edges of the two wings, so as to provide a channel inwardly of the cutting edge along which chips will be transported out of the hole being drilled. The trailing surface of each of the wings is defined by a surface which substantially continuously recedes from the path of the helical edge to the point at which it meets the leading surface of the other wing. This construction provides passageways for chips in the flutes which are of large cross-section and which have substantially no corners or grooves in which chips or other debris can be lodged.

Preferably, the micro drill includes a circumferential land between the helical edge of each wing and the point where the trailing surface of the wing recedes from the path of the helical edge. Preferably, the land on each wing is of a width which subtends an arc of less than about 12°.

The above construction permits the minimization or even the elimination, of back taper with its attendant disadvantages in connection with the possible interference of chips and the lack of support by the hole being drilled of peripheral surfaces of the drill at points remote from the tip.

Now referring to FIGS. 3 and 4, which illustrate one embodiment of a drill body 37 embodying features of the invention, the drill is fabricated from a rigid cylindrical body 37 from suitable materials known to the drill art. The drill material will be dependent upon the material being drilled and the life required for the drill, all as known in the art. As illustrated, two oppositely disposed flutes 39 are provided which helically extend from the drill point 40 along the body 37 towards the shank 41 of the drill. The flutes 39 define a pair of oppositely disposed helically extending wings 43. The helix angle is constant in the illustrated drill. However, depending upon the action required in removing chips it can be varied along the length of the drill to accelerate the removal of chips after they leave the area adjacent the tip of the drill by decreasing the helix angle in the area remote from the tip 40.

Each of the wings 43 has a leading surface 45 in relation to the direction of rotation of the drill, the surface 45 being undercut adjacent its periphery to provide a positive rake helical edge 47. It has been found that a tangent to the face 45 at the helical edge should make an angle of from about 5° to about 30° to a radius 49 of the cylindrical body which too extends the helical edge 47, angle "A" in FIG. 4.

As illustrated, the wings 43 are symmetrically disposed relative to one another to provide a drill web which is generally of "S" shape. In order to cause the chips to be directed inwardly away from the helical edge 47 the leading surface of each wing is formed in a concave shape to provide a channel or trough 51, a substantial portion of which trails the radius 49 which extends to the helical edge 47. Thus, in operation the chips formed by the drilling operation will be moved inwardly by the positive rake helical edge away from the sides of the hole being drilled. In the channel 51, the rotation of the drill causes the chips to be moved out of the drill hole in the flutes 39. Each of the wings 43 is provided with a trailing surface 53 which begins at a periphery of the drill body and substantially continuously recedes from the periphery of the drill body. Preferably, as illustrated, both the leading surfaces 45 and the trailing surfaces 53 are smooth, concave and convex curves, respectively, with a smooth transition therebetween. This results in a structure in which clearance opening between trailing surface 53 and the periphery of the hole being drilled constantly increases along the trailing surface 53 so that there is no area in which chips can be lodged or wedged and the smooth curved surface permits the chips to fall freely against the leading surface 45 of the next following wing along which they are carried out of the drill hole.

For some materials being drilled, particularly those which are relatively soft, it is possible to have the trailing edge 53 begin at the helical edge 47. However, in most instances it is desirable to have a land area 55 which enhances the strength of the helical edge 47. As the land 55 has a curvature which corresponds to the curve transversed by the helical edge 47 and extends from the helical edge rearwardly (based upon the direction of rotation of the drill), it has been determined that the land 55 should preferably subtend an arc "B" of less than about 12°. (See FIG. 4A).

With the above described construction of helical flutes and wings, the drill point 40 may be ground on the end of the drill remote from the shank in the usual manner. As in conventional drills, the point will be ground to provide an angle at the point of from approximately 90° to approximately 120°. The exact angle depends upon the material being drilled, all as known in the art.

In operation, the drill is rotated in the material to be drilled and the chips generated by the tip will move inwardly of the periphery of the hole along the channels provided in the leading edge of each of the wings. The helical edge and its associated land move along the walls of the hole being drilled and have the function of scouring the walls and collecting any chips which might adhere to the walls and move them into the channel 51. Any chips which are not collected by the helical edge and pass between the land and the walls of the hole being drilled have little tendency to become lodged on the smooth convex surface 53 of the trailing edge of the wing but instead are collected and transported out of the hole by the next succeeding wing.

As pointed out above, the cutting edge makes an angle "A" with the radius 49 in the range of from about 5° to about 30°. Preferably, the angle is maintained between about 5° and 15°, and most preferably about 10°.

Drills, as described above, with an appropriate point have been found to drill materials of all types with a minimization of galling and a minimization of wobbling along the drill length as a result of the effective removal of chips.

Figure 5:
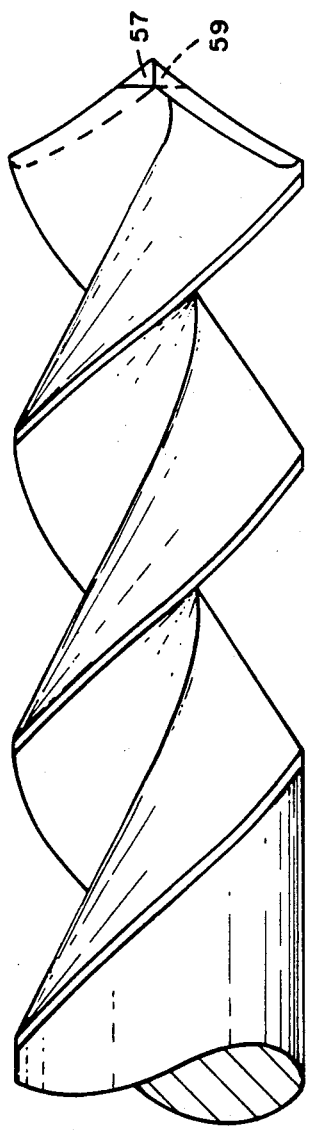
FIG. 5 is a side view of another embodiment of a drill embodying various features of the invention but having a conventional thinned point.

FIGS. 5 and 6 illustrate a drill of the type illustrated in FIGS. 3 and 4, the drill being provided with a so-called split point. This enhances the speed of drilling and aids in drilling an accurate hole. Split points are known in the art and are formed by grinding away a pair of triangular areas as illustrated at 57 and 59 in FIGS. 5 and 6.

The point may also be thinned by other conventional means and used in conjunction with the above described drill body. However, to achieve the best cutting and chip removal, the above described body should be used in conjunction with the drill point described below. Although the drill point and drill body of the present invention act cooperatively to remove chips, it will be understood that either may be used separately, as well.

Figure 7:
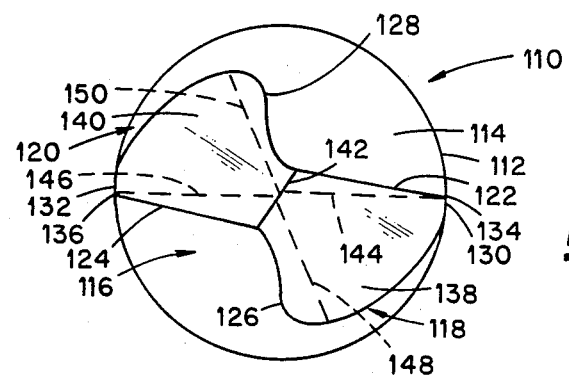
FIG. 7 is an end view of a drill point with dotted lines indicating cut lines on the drill point necessary for forming the micro drill point of the present invention.

There is shown in FIG. 7 an end view of a drill 110 as it would appear prior to being cut or thinned to form the drill point of the present invention. The drill 110 has a generally S-shaped cross-section, but forming a point on the drill 110, as is shown in FIG. 7, distorts, somewhat, the cross-section depending on the point angle. The drill 110 is formed by a generally cylindrical body 112 that has an axis of rotation perpendicular to the plane of the drawing and extending through the center of the body 112. Two flutes 114 and 116 are cut into the cylindrical body 112 in the form of a helix to form two helical wings 118 and 120 which extend helically downwardly along the drill 110. The helix angle of the wings 118 and 120 is about 29°, and preferably ranges between about 15° and 45° depending on the application for the drill. Each wing includes a pair of leading surfaces 122 and 124 and a pair of trailing surfaces 126 and 128. The surfaces 122, 124, 126 and 128 are named in relation to the drilling rotation direction of the drill 110, which rotates counterclockwise as shown in FIG. 7. That is, when the drill 110 is rotated, the leading surface 124 on wing 120 leads the trailing surface 128 and, likewise, leading surface 122 on wing 118 leads the trailing surface 126.

In the preferred embodiment, circumferential lands 130 and 132 are formed along the outermost positions of the wings 118 and 120. Thus, the lands 130 and 132 also extend helically down the drill 110 on the outermost surface of the wings 118 and 120. The intersection of the two lands 130 and 132 with the leading surfaces 122 and 124, respectively, define helical edges 135 and 137 (FIGS. 9-12).

The point of the drill 110 as shown in FIG. 7 includes a pair of flanks 138 and 140 joined at the midregion of the drill 110 by a chisel edge 142. The flanks 138 and 140 are formed by inclined cuts extending from the chisel edge 142 downwardly and outwardly with respect to the drill 110, and leading corners 134 and 136 are defined, respectively, by the intersection of the flanks 138 and 140 and the helical edges 135 and 137. As the drill 110 is shown in FIG. 7, the cutting surfaces of the drill would be the chisel edge 142 and the two edges defined by the intersections of flank 138 and leading surface 122 and by flank 140 and leading surface 124. Preferably, the flank is planar and has a relief angle chosen according to the material of the drill and its intended use.

In the present invention, the drill is cut to modify the cutting edge of the drill 110. In modifying the drill 110 to produce a drill point in accordance with the present invention, a leading portion and a trailing portion are cut from each of the flanks 138 and 140. In the preferred embodiment, the cuts are planar and will intersect the flanks 138 and 140 along the dotted lines as shown in FIG. 7. The cuts will intersect the leading portion of the flanks 138 and 140 along dotted lines 144 and 146, (hereinafter referencing the cutting edges) and the cuts will intersect the trailing portions of the flanks 138 and 140 along dotted lines 148 and 150 (hereinafter referencing the trailing edges).

Figure 8:
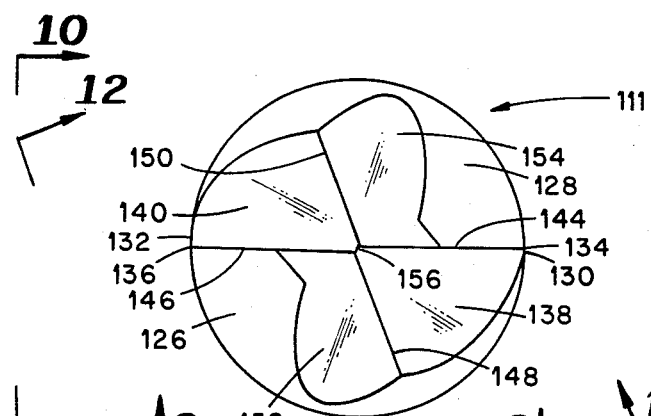
FIG. 8 is an end view of a drill point embodying one form of the present invention.

After the drill point has been cut in accordance with the present invention, a drill 111 as shown in FIG. 8 is formed. The cut produces cutting edges 144 and 146 and trailing edges 148 and 150 on the flanks 138 and 140, and it should be noted that the flanks 138 and 140 both have a reduced surface area with leading and trailing portions of the flanks 138 and 140 being removed. After the drill 110 has been cut, the chisel edge 142 is substantially eliminated from the point of drill 111, and the cutting portions of the drill 111 are the cutting edges 144 and 146.

The cut in the drill 111 has produced side surfaces 152 and 154 which are shown in FIG. 8 as downwardly inclining away from the trailing edges 148 and 150. The surfaces 152 and 154 are primarily on the trailing surfaces 126 and 128 of wings 138 and 140, but are partially formed in the leading surfaces 122 and 124 (not shown in FIG. 8). The cut produces planar surfaces generally beneath the cutting edges 144 and 146, and the flanks 138 and 140. Although most of the chisel edge 142 was removed by the cuts in the point of drill 111, that portion of the chisel edge remaining forms a drill end tip 156 which is shown in FIG. 8. Thus, the cutting structure of the drill 111 at its point includes cutting edges 144 and 146 and the drill end tip 156.

Figure 9:
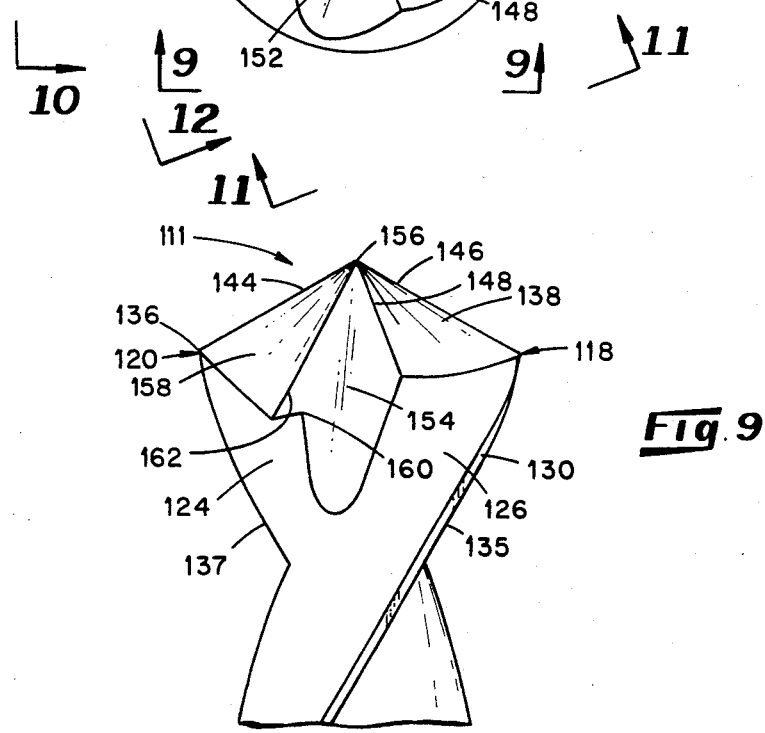
FIG. 9 is a side view of the drill point taken along line 9—9 shown in FIG. 8 and is a view generally perpendicular to the cutting edges of the drill point.

Referring now to FIG. 9, there is shown a side view of the drill 111 taken along lines 9—9 shown in FIG. 8. Basically, this view is taken perpendicularly to the axis of rotation of the drill 111 and perpendicularly to the cutting edges 144 and 146, and shows the somewhat V-shape of the point of drill 111. (As used herein, the term "point" refers to the entire cutting end of the drill 111 and is not a reference to a single position in space.) The point angle, the angle between the cutting edges 144 and 146 is about 120° but may vary depending on the intended application for the drill.

In FIG. 9, the two surfaces formed by the cut in leading surface 124 and trailing surface 126 are shown, and they will be referred to herein as the side surface 154 and the under-surface 158. It will be understood that the cut in leading surface 122 and trailing surface 128 (not shown in FIG. 9) will form surfaces identical to side surface 154 and under-surface 158 on the other side of the drill 111. To avoid duplication, the other side of the drill 111 will not be described in detail herein.

As shown in FIG. 9, the side surface 154 slopes into the plane of the drawing, vertically, from the bottom to the top of surface 154, and, horizontally, from the right to left on surface 154. The under-surface 158 is sloped outwardly with respect to the plane of the drawing, vertically, from the bottom to the top of the surface, and, horizontally, from right to left. The side surface 154 is perpendicular to the under-surface 158 and intersects it along a line 160. The line 160 is sloping outwardly with respect to the plane of the drawing as one travels upwardly along the line. Thus, it will be appreciated that the under-surface 158 forms a cutting edge 144 that provides an increased positive cutting action. That is, the cutting angle presented to a work face is less than ninety degrees along the cutting edge 144 and is sharper, or more acute, than before the drill 111 was cut.

Most of the side surface 154 is cut into the trailing surface 126, but at a corner 160 in the side surface 154, the side surface 154 enters the leading surface 124. The under-surface 158 is cut entirely in the wing 120 and into the leading surface 124 of the drill 111. As shown in FIG. 9, the under-surface 158 inclines outwardly with respect to the plane of the drawing from the intersection of line 160.

Figure 10:
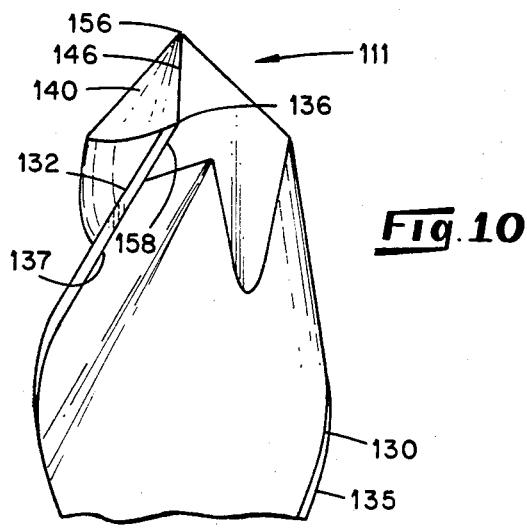
FIG. 10 is a side view of the drill point taken along line 10—10 as shown in FIG. 8 and is a view generally parallel to the cutting edges of the drill point.

In FIG. 10, another side view of the drill 111 is shown taken along the line 10—10 in FIG. 8. This view shows the drill 111 at an angle that is generally parallel to the cutting edge 146 and best shows the leading corner 136. In the preferred embodiment, which is shown in FIG. 10, the horizontal angle of the cutting edge 146 is 30°. The under-surface 158 lies in a plane that includes the leading corner 136, the drill end tip 156 and intersects the axis of rotation of the drill 111 at an acute angle of about, but slightly less than, the helix angle of the drill 111, in this case, about 29°. Thus, the under-surface 158 is cut into the leading surface 124 and "follows" the helix angle of the flute 116.

Figure 11:
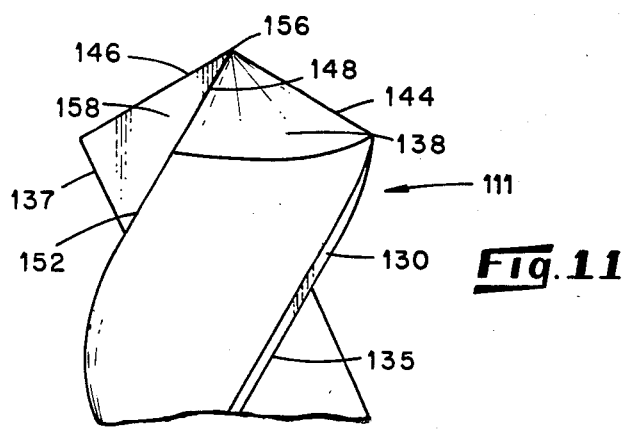
FIG. 11 is a side view of the drill point taken along line 11—11 shown in FIG. 8 and is a view showing the under-surface formed by the cut in the drill point.

Referring now to FIG. 11, there is shown a view of the drill 111 taken along line 11—11 in FIG. 8. In this view, the drill 111 is shown in a direction that is generally parallel to the side surface 152 is perpendicular to horizontal dimensions of under-surface 158 and clearly depicts the inclination of side surface 152. As shown in FIG. 11, the under-surface 158 inclines into the plane of the drawing vertically, from top to the bottom of the surface.

Figure 12:
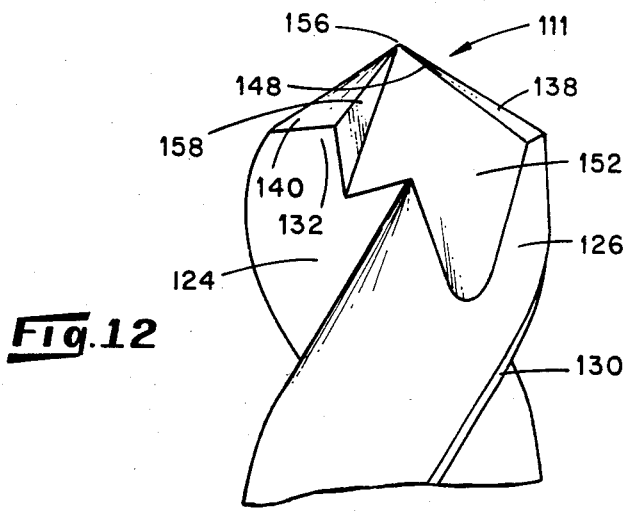
FIG. 12 is a side view of the drill point taken along line 12—12 shown in FIG. 8 and is a view of the side surface formed by the cut in the drill.

Surface 152 lies in a plane that includes the drill end tip 156 and the trailing edge 148 and forms an acute angle of about 29° with the axis of rotation of the drill 111. Again the inclination of surface 152 is chosen to follow the helix angle of the drill 111. As best shown in FIG. 12, trailing edge 148 is inclined at a vertical angle of about 40° with respect to the axis of rotation of the drill 111 and, as best shown in FIGS. 7 and 8, is disposed at a horizontal angular distance of about 40° from the cutting edge 144, but would vary depending on the helix angle of the drill which will dictate the approximate positions of surfaces 152 and 158.

A side view of the drill point 111 is shown in FIG. 12 taken through the line 12—12 of FIG. 8. This view is generally perpendicular to the horizontal dimension of the side surface 152 and, thus, the horizontal dimensions of surface 152 are accurately shown in FIG. 12. The plane of side surface 152 extends through the drill point 156 and, moving in a direction from the drill point 156 downwardly, the plane angles outwardly toward the reader at an angle of about 29° with respect to vertical.

In operation, the drill 111 is rotated in a counter-clockwise direction as viewed from the point of the drill 111 so that the cutting edges 144 and 146 are raked across a work face of the material being drilled. The edges 144 and 146 cut chips of material from the work face which are thrown upwardly because of the positive cutting angle of the cutting edges 144 and 146. The increased positive cutting action provided by the under-surface 158 increases the upward thrust of the cut chips and results in more rapid and more certain removal of the chips from a work face. Also, that portion of the trailing surfaces removed along the side surface 154 provides an increased size in the passageway for carrying away the chips. After the chips leave the area of the under-surface 158, the flutes 114 and 116 carry the chips upwardly out of the bore being formed by the drilling operation.

Referring to FIGS. 7 and 8, it will be appreciated that the cuts forming the cutting edges 144 and 146 and the trailing edges 148 and 150 will reduce the area of the flanks 138 and 140. Thus, the flank area of drill 111 is less than the flank area of drill 110. The reduced flank area tends to reduce the likelihood of burring or heeling at the workface. Also, the added cuts in the drill 111 relative to drill 110 results in the virtual elimination of the chisel edge 142. Cutting edges 144 and 146, which have positive cutting angles, replace chisel edge 142 which had a negative cutting angle and tended to grind, instead of cut, the workface. Thus, the drill 111 of the present invention has almost entirely positive cutting at the drill point which results in more efficient drilling and, generally, a longer drill life.

Although a preferred embodiment of the invention has been described above in connection with FIGS. 1–12, it will be understood that the invention is capable of modification without departing from the spirit of the invention. In particular, it will be noted that the various angular cuts in the drill 111, such as those forming the flanks 138 and 140, the under-surface 158, and the side surfaces 154, will vary according to the type of material from which the drill is constructed, the type of the material to be cut and the size of the drill. Typically, the point angle (the angle between cutting edge 144 and edge 146) may vary, but usually will be about 120°. Preferably the cut in the drill 111 will provide an under-surface 158 that passes through the leading corner 136 and through the drill end tip 156, but it will be understood that the surface could also lie near, but not through, those two points. The inclination angle of surface 158 may also vary, but preferably, the acute angle formed between surface 158 and the axis of rotation of the drill 111 will be about 29°, that is, the helix angle of the drill. Likewise, the inclination angle between the side surface 154 and the axis of rotation of the drill 111 preferably is about 29° which is the helix angle.

The helix angle of the drill 111 is 29° and preferably is within a range of 15° to 45°. However, it will be understood that the present invention is applicable to all micro drills regardless of helix angle, and that as the helix angles change, the position and angles of surfaces 152 and 158 will vary accordingly.

What is claimed is:
1. An improved micro drill comprising:
 a rigid cylindrical body having a center axis of rotation;
 a drill point formed on one end of said body with the center of said drill point lying on the axis of rotation of said rigid cylindrical body;
 two oppositely disposed flutes helically extending from about said drill point along said body;
 two oppositely disposed helically extending wings being defined by said flutes;
 a leading surface in relation to the direction of rotation of said body formed on each of said wings;
 a helical edge being defined along the outermost positions of each of said leading surfaces;
 a trailing surface formed on each of said wings and trailing said leading surface relative to the rotation direction of said body, said trailing surface on one of said wing being connected with the leading surface of the other of said wings;
 two opposed flanks formed on said drill point by an inclined cut in each of said wings extending from the center of said drill point downwardly into the cylindrical body and outwardly toward the periph- ery of said cylindrical body, said inclined cuts providing said drill point with a somewhat V-shape;

a leading corner being defined on each of said wings at the intersection of said helical edge and said flanks;

a leading cut formed in each of said wings through said flanks to remove at least a portion of said flanks adjacent to said leading surfaces, said leading cuts and said flanks intersecting to define cutting edges on said drill point that extend from about the center of said point to about said leading corners on said flank, said leading cuts forming planar surfaces below said flanks and forming substantially linear cutting edges at the intersection of said planar surface and said flanks.

2. An improved micro drill comprising:

a rigid cylindrical body having a center axis of rotation;

a drill point formed on one end of said body with the center of said drill point lying on the axis of rotation of said rigid cylindrical body;

two oppositely disposed flutes helically extending from about said drill point along said body;

two oppositely disposed helically extending wings being defined by said flutes;

a leading surface in relation to the direction of rotation of said body formed on each of said wings;

a helical edge being defined along the outermost positions of each of said leading surfaces;

a trailing surface formed on each of said wings and trailing said leading surface relative to the rotation direction of said body, said trailing surface on one of said wing being connected with the leading surface of the other of said wings;

two opposed flanks formed on said drill point by an inclined cut in each of said wings extending from the center of said drill point downwardly into the cylindrical body and outwardly toward the periphery of said cylindrical body, said inclined cuts providing said drill point with a somewhat V-shape;

a leading corner being defined on each of said wings at the intersection of said helical edge and said flanks;

a leading cut formed in each of said wings through said flanks to remove at least a portion of said flanks adjacent to said leading surfaces, said leading cuts and said flanks intersecting to define cutting edges on said drill point that extend from about the center of said point to about said leading corners on said flank, said leading cuts forming a planar surface in each of said wings that passes approximately through the center of said drill point and said leading corner and forming an angle of about the helix angle with the axis of rotation of said cylindrical body.

3. An improved micro drill comprising:

a rigid cylindrical body having a center axis of rotation;

a drill point formed on one end of said cylindrical body with the center of said drill point lying on the axis of rotation of said cylindrical body;

two oppositely disposed flutes helically extending from about said drill point along said cylindrical body at a helix angle;

a pair of oppositely disposed helically extending wings being formed by said flutes and being disposed at the helix angle;

a leading surface in relation to the direction of rotation of said cylindrical body being formed on each of said wings;

a helical edge being defined along the outermost positions of each of said leading surfaces;

a circumferential land defining the periphery of said body and trailing said helical edge relative to the rotation direction of said cylindrical body;

a trailing surface on each of said wings continuously receeding from said circumferential land and trailing said circumferential land relative to the rotation direction of said cylindrical body, said trailing surface of one wing meeting said leading surface of the other wing at about the midregion of said cylindrical body;

two opposed flanks formed on said drill point by inclined cuts in each of said wings extending from about the center of said drill point downwardly into said cylindrical body and outwardly toward the periphery of said cylindrical body;

a leading corner formed on each wing at the drill point by the intersection of said helical edge and said flank;

a planar under-surface formed in each wing adjacent the leading surface thereof and extending from about the center of said drill point to about said leading corner;

each of said planar under-surfaces lying in a plane extending through about the center of said drill point and about said leading corner and forming an acute angle of about the helix angle with the axis of rotation of said cylindrical body;

said planar under-surfaces forming cutting edges having a positive cutting angle and extending from about the center of said drill point to each of said leading corners;

a planar side surface formed in each of said trailing surfaces and said connected leading surfaces, each of said planar side surfaces lying in a plane extending through about the center of said drill point, forming an acute angle of about the helix angle with the axis of rotation of said cylindrical body and intersecting said flanks to form trailing edges extending from about the center of said drill point along the surface of said flank; and each of said planar side surfaces being substantially perpendicular to one of said under-surfaces.

4. A micro drill comprising:

a rigid cylindrical body;

a drill point formed at one end of said body;

two oppositely disposed flutes formed in said body and helically extending from said drill point along said body and having a transverse cross-section of generally S-shape;

a pair of oppositely disposed helically extending wings being defined on said body by said flutes and defining a web at the center of the drill;

a pair of helical edges disposed on the periphery of said body at said wings;

a leading surface, in relation to the direction of rotation of the drill, formed in a substantially continuous smooth concave curve on each of said wings and extending from said helical edge generally toward the axis of rotation of the drill;

a trailing surface, in relation to the direction of rotation of the drill, formed in a substantially continuous smooth convex curve on each of said wings and defining a curve which substantially continuously recedes from said helical edge of said wing and meets the leading surface of the other wing;

a smooth transition formed between said trailing surface of each of said wings and the leading surface of each of the other wings;

a circumferential land formed on each wing extending from and trailing said helical edge of said wing, each of said circumferential lands subtending a radial arc of less than about 12° from the center axis of said body;

a helical channel formed in each of said leading surfaces, said helical channel trailing relative to the direction of rotation of the drill, a radius of the drill over a substantial portion of the radial dimension of the drill, said helical channel being operable to facilitate the removal of shavings and chips from the drill during use;

an undercut formed in each of said leading surfaces so that said cutting edges have a positive rake and make an angle from about 5° to about 30° to a radius of said cylindrical body which extends to said cutting edge;

two opposed flanks formed on said drill point by an inclined cut in each of said wings extending from the center of said drill point downwardly into the cylindrical body and outwardly toward the periphery of said cylindrical body, said inclined cuts providing said drill point with a somewhat V-shape;

leading corners being defined on said wings at the intersection of said helical edges and said flanks; and leading cuts formed in said wings through said flanks to remove at least a portion of said flanks adjacent to said leading surfaces, said leading cuts and said flanks intersecting to define cutting edges on said drill point that extend from about the center of said point to about said leading corners on said flanks.

* * * * *

UNITED STATES PATENT AND TRADEMARK OFFICE
CERTIFICATE OF CORRECTION

PATENT NO. : 4,602,900

DATED : July 29, 1986

INVENTOR(S) : Jerry Arpaio, Jr. and Derek E. Heath

It is certified that error appears in the above-identified patent and that said Letters Patent is hereby corrected as shown below:

Column 1, line 46, "samll" should be -- small --.

Column 1, line 50, "drlling" should be -- drilling --.

Column 2, line 41, "drlls" should be -- drills --.

Column 10, line 22, "under-surface" should be -- under-surfaces --.

Signed and Sealed this

Thirtieth Day of December, 1986

Attest:

DONALD J. QUIGG

Attesting Officer

Commissioner of Patents and Trademarks